United States Patent [19]

Contamin et al.

[11] Patent Number: 4,765,922
[45] Date of Patent: Aug. 23, 1988

[54] SKIN CLEANSING COMPOSITION IN THE FORM OF A ROD OR STICK COMPRISING A LACTATE

[75] Inventors: Jean-Claude Contamin, Chilly Mazarin; Roberte Latapie, Ablon S/Seine, both of France

[73] Assignee: L'Oreal, Paris, France

[21] Appl. No.: 97,828

[22] Filed: Sep. 17, 1987

[30] Foreign Application Priority Data

Sep. 30, 1986 [FR] France ................. 86 13604

[51] Int. Cl.$^4$ ................. C11D 9/30; C11D 17/00
[52] U.S. Cl. ................. 252/90; 252/134; 252/174; 252/174.17; 252/547; 252/DIG. 5; 424/DIG. 5
[58] Field of Search .......... 424/DIG. 5; 252/547, 252/528, 174.17, 120, 134, 90, DIG. 5, 174; 514/614, 616

[56] References Cited

U.S. PATENT DOCUMENTS 3,098,795  7/1963  Kreps ................. 167/90
4,380,549  4/1983  Van Scott ................. 424/317
4,548,810 10/1985  Zofchak ................. 424/59

FOREIGN PATENT DOCUMENTS 0007785  2/1980  European Pat. Off. .

Primary Examiner—Paul Lieberman
Assistant Examiner—Kathleen Markowski
Attorney, Agent, or Firm—Cushman, Darby & Cushman

[57] ABSTRACT

A skin cleansing composition, in the form of a rod or stick, contains a fatty phase, a water phase and a consistency agent. The consistency agent is a mixture of at least one fatty acid having 12 to 22 carbon atoms and a lactate of the formula:

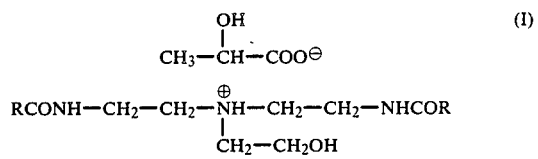

wherein R represents an alkyl or alkenyl radical having 13 to 17 carbon atoms or a mixture consisting essentially of said alkyl and/or alkenyl radicals.

6 Claims, No Drawings

SKIN CLEANSING COMPOSITION IN THE FORM OF A ROD OR STICK COMPRISING A LACTATE

The present invention relates to a cosmetic composition for cleansing the skin so as to remove soil, oily material and dead cells present thereon.

Facial skin periodically requires cleansing in order to remove not only oily substances resulting from the use of make-up products, but also dead skin caused by epidermis desquamation.

Cleansing of the skin can be carried out by various procedures depending on the effect desired.

For instance, detergent preparations can be employed but these preparations exhibit a certain tendency to dry the skin without necessarily removing all undesirable substances from the face.

Abrasive containing compositions have also been proposed but these compositions, even if they are particularly effective, they nonetheless are irritating to the skin.

Moreover, it has been noted that the use of lotions or liquid compositions is not always appropriate especially when cleansing certain parts of the face and particularly when cleansing those areas around the eyes.

The present invention, however, provides a new cleansing composition in the form of a rod or stick which is easy to apply to the skin without encountering the disadvantages of known compositions.

More precisely, the composition in accordance with the present invention permits selective cleansing of the face and leaves the skin, after use, particularly smooth and soft.

The composition according to the present invention is capable of cleansing the skin by removal of oily substances, soil and dead skin by an agglutinating or binding effect or even by rinsing the thus treated face with water, leaving the skin fresh and clean.

The present invention thus relates to, as a new industrial product, a skin cleansing composition, in the form of a rod or stick, consisting essentially of a fatty phase, a water phase and a consistency phase, the latter being a mixture of at least one fatty acid having 12 to 22 carbon atoms and a lactate of the formula

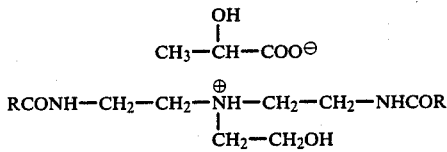

(I)

wherein

R represents an alkyl or alkenyl radical having 13 to 17 carbon atoms or a mixture consisting essentially of such alkyl and/or alkenyl radicals.

In the cleaning composition, according to the present invention, which have a continuous aqueous phase, the water phase represents from 20 to 70 weight percent and the fatty phase represents from 15 to 65 weight percent, based on the total weight of the composition.

The fatty acid present in the consistency phase is employed to achieve the rod or stick form of the composition and is generally present in an amount ranging from 0.5 to 10% and preferably from 1 to 5%, by weight, based on the total weight the composition. This fatty acid is selected from the group consisting of myristic acid, palmitic acid, stearic acid, oleic acid, linoleic acid, and mixtures thereof.

The lactate of Formula I is generally present in combination with the fatty acid, in an amount ranging from 1.5 to 6 weight percent and preferably from 2 to 5 weight percent, based on the total weight of the composition.

In accordance with a preferred embodiment of the invention, the lactate of Formula I, is a product sold under the tradename "EMPIGEN FKH 100/L" by Marchon France S.A.

This product corresponds to Formula I above wherein R represents the residue of a mixture of fatty acids having essentially the following composition:

| | |
|---|---|
| $C_{14}$ | ≈2% |
| $C_{16}$ | ≈22% |
| $C_{16}$ (mono-unsaturated) | ≈5% |
| $C_{18}$ | ≈8% |
| $C_{18}$ (mono-unsaturated) | ≈40% |
| $C_{18}$ (di-unsaturated) | ≈20% |
| and others | ≈3% |

Various tests which have been carried out demonstrate that the presence of both the fatty acid and the lactate of Formula I are quite critical in obtaining a composition in the form of a rod or stick.

The fatty phase of the composition of the present invention comprises an oil and preferably at least one oil and one wax.

Representative oils usefully employed as fatty phase include the following:

(1)—mineral oils: paraffin oil, petrolatum oil and mineral oils having a boiling point between 310 and 410° C.;

(2)—oils of animal origin: purcellin oil and perhydrosqualene;

(3)—vegatable oils: sweet almond oil, palm oil, callophylum oil, avocado oil, olive oil, ricin oil and oils of cereal germs, such as wheat germ oil;

(4)—silicon oils: dimethyl polysiloxane;

(5)—sythetic esters: butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate, propylene glycol dicaprylate and di-isopropyl adipate;

(6)—organic alcohols: oleyl alcohol, linoleic alcohol, linolenic alcohol, isostearyl alcohol and octyl dodecanol; and (7)—esters derived from lanolin acid: isopropyl lanolate and isocetyl lanolate.

Representative waxes include:

(1)—mineral waxes: microcrystalline wax, paraffin wax and petrolatum wax;

(2)—fossil waxes: ozokerite and montan wax;

(3)—waxes of animal origin: beeswax, spermaceti, lanolin wax, lanolin derivatives such as lanolin alcohol, hydrogenated lanolin, hydroxylated lanolin, acetylated lanolin, fatty acid of lanolin and acetylated lanolin alcohol;

(4)—waxes of vegetable origin: candellila wax, carnauba wax, Japan wax and cocoa butter;

(5)—hydrogenated oils solid at 25° C.: hydrogenated ricin oil, hydrogenated palm oil, hydrogenated tallow, hydrogenated cocoa oil and hydrogenated soya oil;

(6)—synthetic waxes: polyethylene waxes and copolymerized polyethylene waxes;

(7)—fatty esters solid at 25° C.: propyleneglycol monomyristate and myristyl myristate; and (8)—silicone waxes: methyloctadecane-oxypolysiloxane poly dimethylsiloxy stearoxysiloxane.

In accordance with a preferred embodiment of the compositions of the present invention the fatty phase consist essentially of paraffin, this type of composition providing a cleansing of the skin of a binding or agglutinating effect.

The composition according to the present invention can also contain an emulsifier which can be present in an amount ranging from 1 to 30 weight percent and preferably from 3 to 25 weight percent, based on the total weight of the composition. These emulsifier-containing rods or sticks are more particularly employed in situations where, after application to the face, the face is then washed or rinsed with water.

Representative emulsifiers include, in particular, soaps of faty acids, polyglycerol alkylethers, glycerol stearates, esters of sorbitan and fatty acids, oxyethylenated or not, in particular polyoxyethylenated sorbitan monostearate and monolaurate, sorbitan oleates such as sorbitan monooleate or sorbitan trioleate, polyoxyethylenated fatty alcohols and the esters of phosphoric acid and ethoxylated fatty alcohols.

The composition according to the present invention can also contain other substances as complementary components such as, for example, perfumes, coloring agents, preservatives, keratolytic agents and anti-oxidants.

The following non-limiting examples are given to illustrate the present invention.

EXAMPLE 1

In accordance with the invention an exfoliative stick for cleaning the face is prepared having the following composition:

| | |
|---|---|
| Stearic acid | 4 g |
| Paraffin | 20.7 g |
| Empigen FKH 100/L | 5 g |
| Triethanol amine | 0.6 g |
| Preservatives | 0.3 g |
| Veegum K | 1.5 g |
| Coloring agent, sufficient amount | |
| Perfume, sufficient amount | |
| Water, sufficient amount for | 100 g |
| This stick, when applied to facial skin, cleanses the same by a binding effect. | |

EXAMPLE 2

In accordance with the invention a toilet cream in the form of a stick is prepared having the following composition:

| | |
|---|---|
| Glycerol monostearate and polyoxyethylenated stearate | 8 g |
| Stearic acid | 2 g |
| Palmitic acid | 2 g |
| Sorbitan monostearate oxyethylenated with 20 moles of ethylene oxide | 2 g |
| Cetyl alcohol | 1 g |
| Petrolatum oil | 40 g |
| Sorbitan monolaurate oxyethylenated with 20 moles of ethylene oxide | 3 g |
| Empigen FKH 100/L | 5 g |
| Preservatives | 0.3 g |
| Perfume, sufficient amount | |
| Water, sufficient amount for | 100 g |

After applying the cream and massaging the face, the face is then rinsed with water. The skin is clean and exhibits a firm and smooth appearance.

EXAMPLE 3

In accordance with the invention a stick is prepared containing the following components:

| | |
|---|---|
| Myristic acid | 3 g |
| Carnauba wax | 23 g |
| Empigen FKH 100/L | 2 g |
| Sodium hydroxide | 0.3 g |
| Preservative | 0.3 g |
| Bentonite | 2 g |
| Coloring agent, sufficient amount | |
| Perfume, sufficient amount | |
| Water, sufficient amount for | 100 g |

After application to facial skin it is noted that the face is clean and has a soft appearance.

What is claimed is:

1. A cosmetic skin cleansing composition, in the form of a rod or stick, comprising a fatty phase, a water phase and a consistency agent, the said consistency agent being a mixture of at least one fatty acid having 12 to 22 carbon atoms and a lactate of the formula

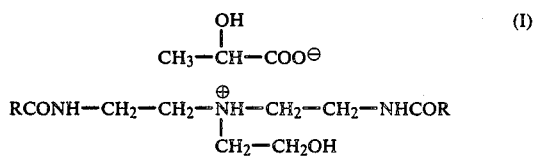

wherein
R represents alkyl or alkenyl radicals having 13 to 17 carbon atoms or a mixture consisting essentially of said alkyl and/or alkenyl radicals and wherein said water phase is present in an amount ranging from 20 to 70 weight percent, said fatty phase is present in an amount ranging from 15 to 65 weight percent, said fatty acid is present in an amount ranging from 0.5–10 weight percent and said lactate is present in an amount ranging from 1.5 to 6 weight percent, based on the total weight of the composition.

2. The composition of claim 1 wherein said fatty acid having 12 to 22 carbon atoms is selected from the group consisting of myristic acid, palmitic acid, stearic acid, oleic acid, linoleic acid and mixtures thereof.

3. The composition of claim 1 wherein said fatty acid is present in an amount ranging from 1 to 5 percent by weight based on the toral weight of said composition.

4. The composition of claim 1 wherein said lactate is present in an amount ranging from 2 to 5 percent by weight based on the total weight of said composition.

5. The composition of claim 1 which also contains at least one of a perfume, a coloring agent, a preservative, a keratolytic agent or an antioxidant.

6. A process for cleansing facial skin comprising applying thereto an amount, effective to clean the skin, of the composition of claim 1.

* * * * *